(12) United States Patent
Nofsinger et al.

(10) Patent No.: US 10,702,372 B2
(45) Date of Patent: Jul. 7, 2020

(54) REVERSIBLE ANCHORING DEVICES

(71) Applicant: University of South Florida, Tampa, FL (US)

(72) Inventors: Charles Cole Nofsinger, Land O'Lakes, FL (US); Summer Joy Decker, Apollo Beach, FL (US); Jonathan Michael Ford, Apollo Beach, FL (US); William E. Lee, St. Petersburg, FL (US); Charli H. Regel, Pinellas Park, FL (US); Mahmoud Y. Dweik, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/326,290

(22) PCT Filed: May 21, 2015

(86) PCT No.: PCT/US2015/031974
§ 371 (c)(1),
(2) Date: Jan. 13, 2017

(87) PCT Pub. No.: WO2016/010628
PCT Pub. Date: Jan. 21, 2016

(65) Prior Publication Data
US 2017/0202659 A1   Jul. 20, 2017

Related U.S. Application Data

(60) Provisional application No. 62/024,668, filed on Jul. 15, 2014.

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 17/0487* (2013.01);
(Continued)

(58) Field of Classification Search
CPC ........ A61B 17/0401; A61B 2017/0453; A61B 2017/044; A61B 2017/0414;
(Continued)

(56) References Cited

U.S. PATENT DOCUMENTS 4,537,185 A   8/1985   Stednitz
4,950,270 A   8/1990   Bowman
(Continued)

OTHER PUBLICATIONS

Kamelger, et al., "Suspensory fixation of grafts in anterior cruciate ligament reconstruction: a biomechanical comparison of 3 implants", Arthroscopy: The Journal of Arthroscopic & Related Surgery 25.7 (2009): 767-76.
(Continued)

*Primary Examiner* — Christopher R Harmon
(74) *Attorney, Agent, or Firm* — Thomas | Horstemeyer, LLP

(57) ABSTRACT

In one embodiment, a reversible anchoring device includes a base having a threaded shaft and an internal passage that extends through the base along a longitudinal direction of the base and a cap having a top surface, a bottom surface, a threaded circular opening formed in the bottom surface adapted to thread onto the threaded shaft of the base, and a suture opening that extends from the top surface of the cap to the threaded circular opening through which a suture can pass.

14 Claims, 7 Drawing Sheets

(52) U.S. Cl.
CPC .............. *A61B 2017/0404* (2013.01); *A61B 2017/0414* (2013.01); *A61B 2017/0453* (2013.01); *A61F 2002/0829* (2013.01); *A61F 2002/0864* (2013.01); *A61F 2002/0882* (2013.01)

(58) Field of Classification Search
CPC .... A61B 2017/0404; A61B 2017/0445; A61B 2017/045; A61B 2017/0456; A61B 2017/0458; A61B 2017/0459; A61B 2017/0496; A61F 2/0811; A61F 2002/0829; A61F 2002/0864
See application file for complete search history.

(56) References Cited

U.S. PATENT DOCUMENTS

| | | |
|---|---|---|
| 5,156,616 A | 10/1992 | Meadows |
| 5,702,397 A | 12/1997 | Goble |
| 6,994,725 B1 | 2/2006 | Goble |
| 7,147,652 B2 | 12/2006 | Bonutti |
| 7,491,217 B1 | 2/2009 | Hendren |
| 7,833,244 B2 | 11/2010 | Cerundolo |
| 9,084,596 B2* | 7/2015 | Stanley ............. A61B 17/0401 |
| 9,402,622 B2* | 8/2016 | Taylor ............... A61B 17/0487 |
| 2007/0073291 A1* | 3/2007 | Cordaro ............ A61B 17/7032 606/86 A |
| 2009/0292321 A1 | 11/2009 | Collette |
| 2012/0041496 A1 | 2/2012 | Walker |
| 2012/0065648 A1 | 3/2012 | Roorda |
| 2013/0035720 A1 | 2/2013 | Perriello |
| 2013/0331896 A1* | 12/2013 | Holt ................... A61B 17/0487 606/328 |
| 2014/0081323 A1* | 3/2014 | Hawkins ........... A61B 17/0401 606/232 |
| 2014/0194907 A1 | 7/2014 | Bonutti et al. |

OTHER PUBLICATIONS

European Search Report for Application No. 15821573.1-1122 dated Mar. 26, 2018, 7 pages.

* cited by examiner

REVERSIBLE ANCHORING DEVICES

CROSS-REFERENCE TO RELATED APPLICATION

This application claims priority to U.S. Provisional Application Ser. No. 62/024,668, filed Jul. 15, 2014, which is hereby incorporated by reference herein in its entirety.

BACKGROUND

In the typical anterior cruciate ligament (ACL) reconstruction via suspensory fixation, a graft tendon is pulled into a passage formed in the femur with sutures and the sutures are anchored in place within the bone using a suspensory button anchoring device. In this process, the anchoring device is also passed through the passage and, once positioned in the desired position, deployed to lock the device in place within the bone.

While the above-described anchoring devices are viable, they have several drawbacks. First, the devices are relatively expensive, which increases the overall cost of the procedure. Second, the devices can be difficult to pass through the femur and deploy in the desired location. Third, the devices can loosen over time, which results in loosening of the graft. Fourth, the devices are permanent in that they cannot be repositioned after they have been deployed.

From the above discussion, it can be appreciated that it would be desirable to have an anchoring device that avoids one or more of the above-described drawbacks.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

Figure 1:
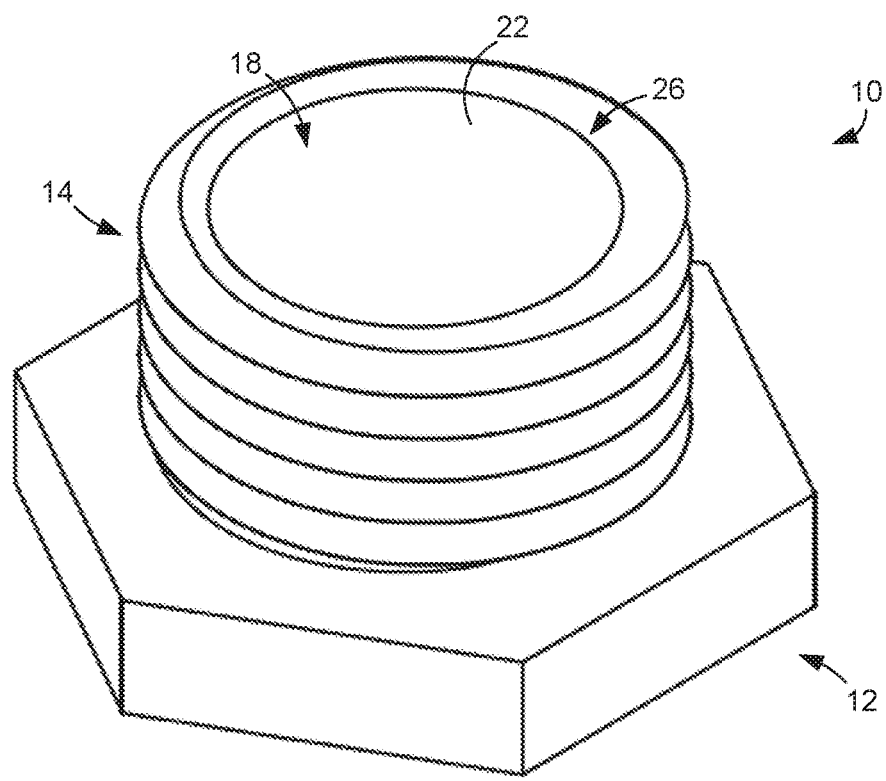
FIG. 1 is a top perspective view of an embodiment of a base of a reversible anchoring device.
Figure 2:
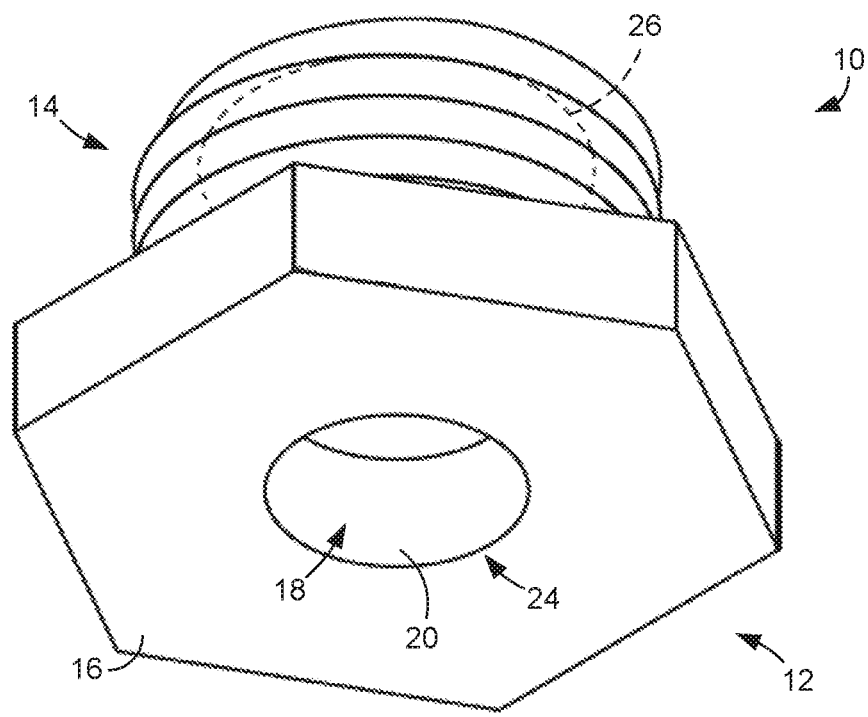
FIG. 2 is a bottom perspective view of the base of FIG. 1.
Figure 3:
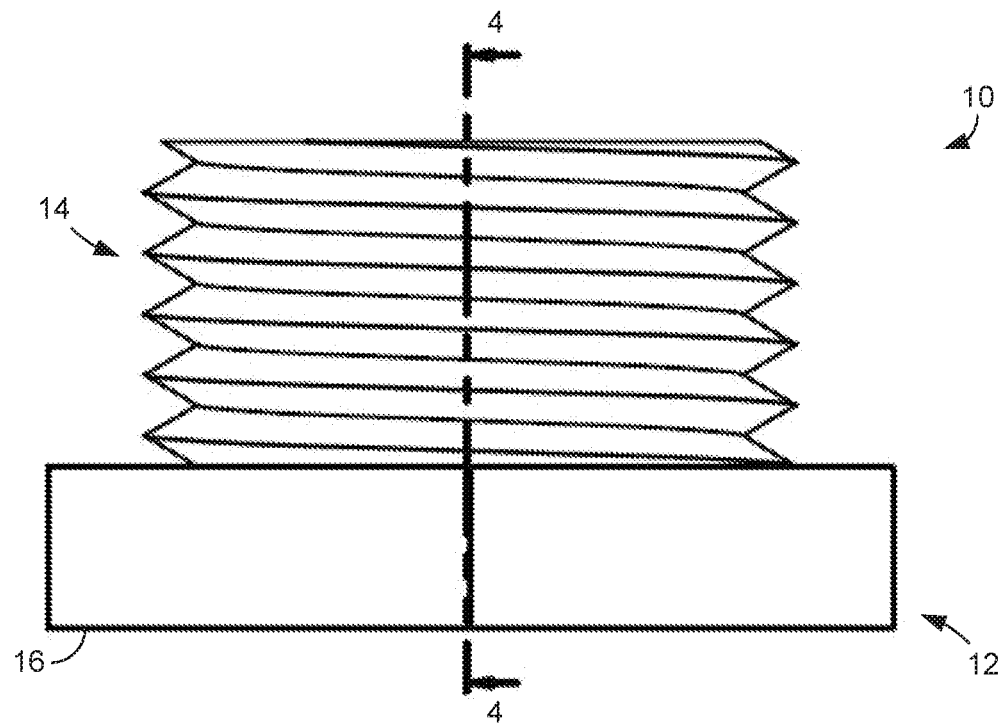
FIG. 3 is a side view of the base of FIG. 1.
Figure 4:
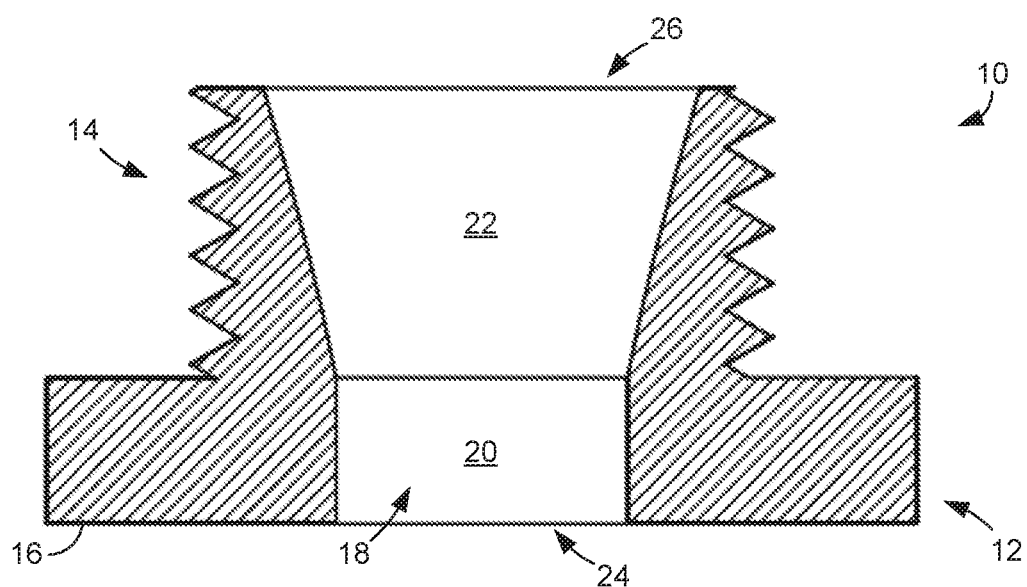
FIG. 4 is a side cross-sectional view of the base of FIG. 1 taken along line 4—4 shown in FIG. 3.

As described above, it would be desirable to have an anchoring device that avoids one or more drawbacks of suspensory button anchoring devices. Disclosed herein are reversible anchoring devices that, for example, can be used to secure a graft tendon in an anterior cruciate ligament (ACL) reconstruction procedure. In some embodiments, the anchoring device includes a base and a cap that are adapted to be threaded together. In use, the base is positioned on the surface of the femur at the opening of a passage that has been formed through the femur. The ends of a suture that is attached to a graft tendon are pulled through the passage from bottom to top and are passed through an opening in the base. The suture is then passed through one or more openings formed in the cap and the cap is securely threaded onto the base to form an anchoring device that compresses the suture and prevents it from moving relative to the device.

In the following disclosure, various specific embodiments are described. It is to be understood that those embodiments are example implementations of the disclosed inventions and that alternative embodiments are possible. All such embodiments are intended to fall within the scope of this disclosure.

FIGS. 1-9 illustrate components of an embodiment of a reversible anchoring device. More particularly, FIGS. 1-4 illustrate a base 10 of the device while FIGS. 5-9 illustrate a cap 30 of the device, both of which can be made of a biocompatible metal, such as stainless steel or titanium.

As illustrated in FIGS. 1-4, the base 10 is generally configured as a threaded bolt. Accordingly, the base 10 comprises a hexagonal head 12 from which extends a threaded shaft 14. The head 12 and shaft 14 are both relatively small in size. By way of example, the head 12 is approximately 7 to 12 mm wide (from one facet to an opposite facet) and the shaft 14 is approximately 5 to 10 mm in diameter and approximately 5 to 7 mm in length. As indicated in the figures, the head 12 defines a bottom surface 16 of the base 10, which is adapted to contact the outer surface of the femur when the anchoring device is implanted.

Unlike a conventional bolt, the base 10 includes an internal passage 18 that extends through the head 12 and the shaft 14 along a longitudinal direction of the base. As shown most clearly in the cross-sectional view of FIG. 4, the passage 18 includes a first portion 20 associated with the head 12 and a second portion 22 associated with the shaft 14. In the illustrated embodiment, the first portion 20 is generally cylindrical (i.e., has a generally constant diameter along its length direction) while the second portion is frustoconical (i.e., has as expanding diameter along its length direction). The frustoconical portion expands in diameter in a direction away from the head 12. As described below, the frustoconical portion 22 is used to secure the ends of a suture that has been passed through the internal passage 18. As is further shown in FIG. 4, the internal passage 18 includes a first or bottom opening 24 and a second or top opening 26, which both provide access to the passage.

FIGS. 5-9 illustrate the cap 30 that, with the base 10, forms the anchoring device. As shown in these figures, the cap 30 is generally cylindrical and includes a first or bottom surface 32 and a second or top surface 34. Formed in the bottom surface 32 of the cap 30 is a threaded circular opening 36 that is adapted to thread onto the threaded shaft 14 of the base 10. As is most clearly illustrated in the cross-sectional view of FIG. 9, the threaded circular opening 36 extends into the body of cap 30 a distance approximately three-quarters of the way to the top surface 34. As is also apparent from FIG. 9, the cap 30 includes a central frustoconical member 38 within the opening 36 that extends from the bottom of the threaded circular opening 36 to the bottom surface 32 of the cap. This frustoconical member 38 is sized and configured to be received by the frustoconical portion 22 of the internal passage 18 of the base 10 with little clearance between the member and the passage.

Figure 5:
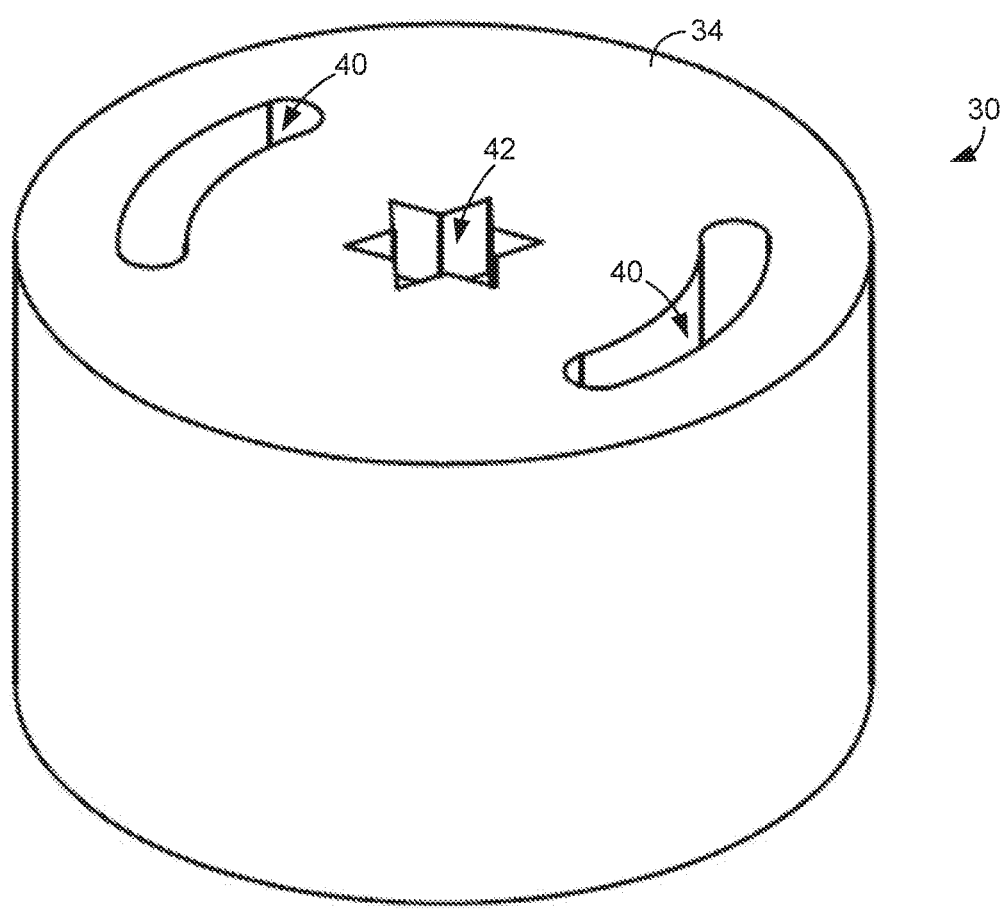
FIG. 5 is a top perspective view of an embodiment of a cap designed to be used with the base of FIG. 1.
Figure 6:
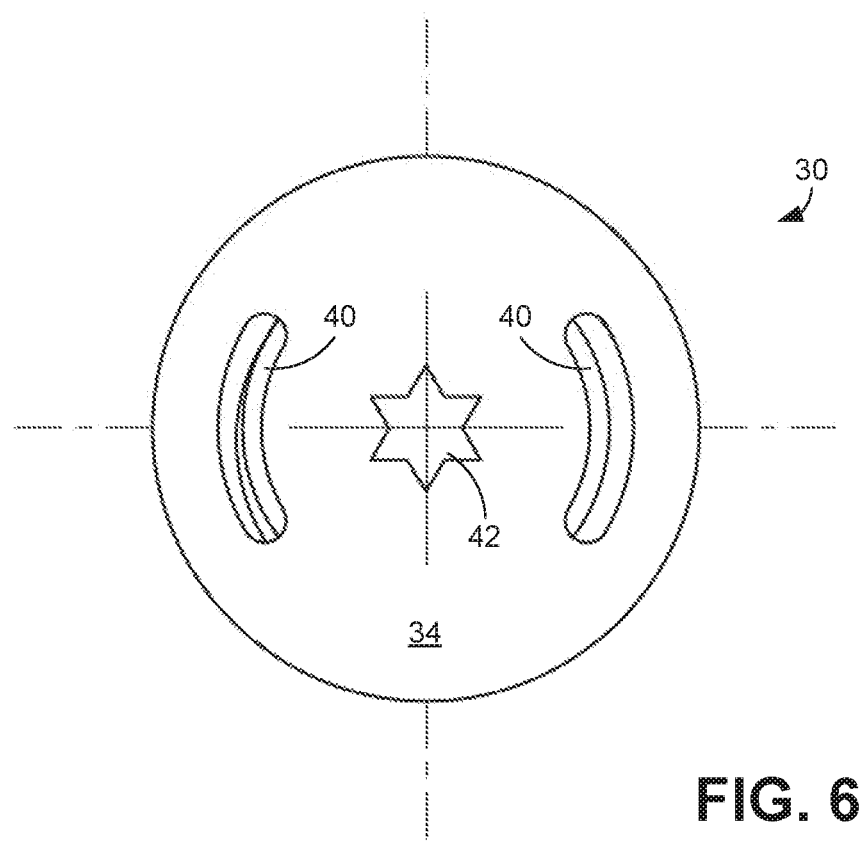
FIG. 6 is a top view of the cap of FIG. 5.
Figure 7:
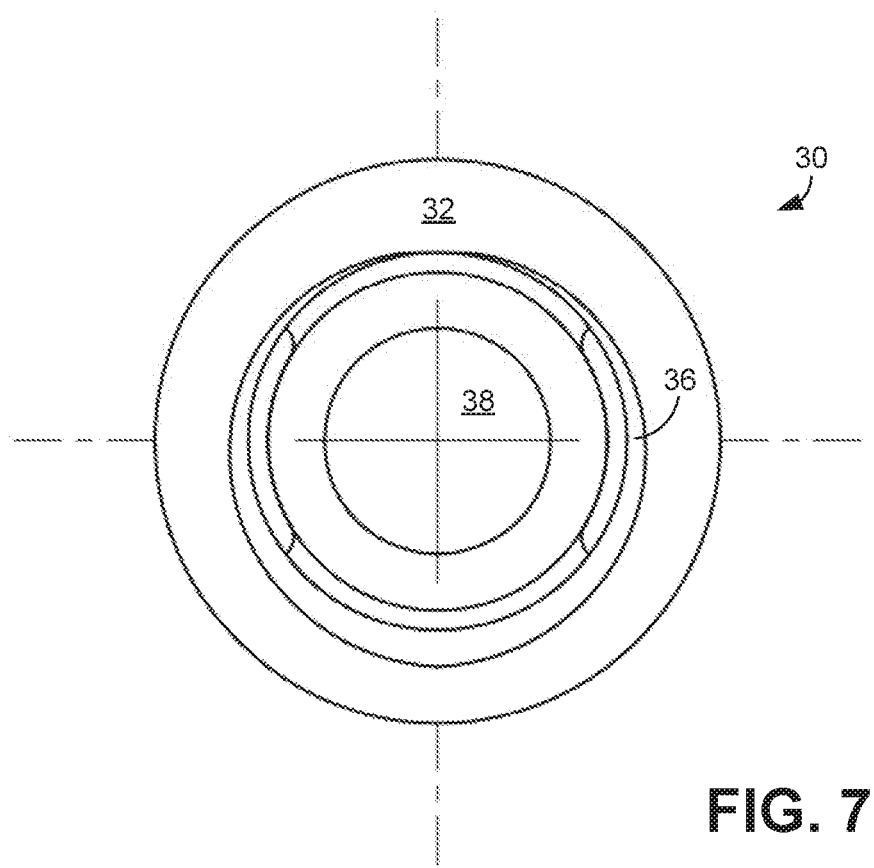
FIG. 7 is a bottom view of the cap of FIG. 5.
Figure 8:
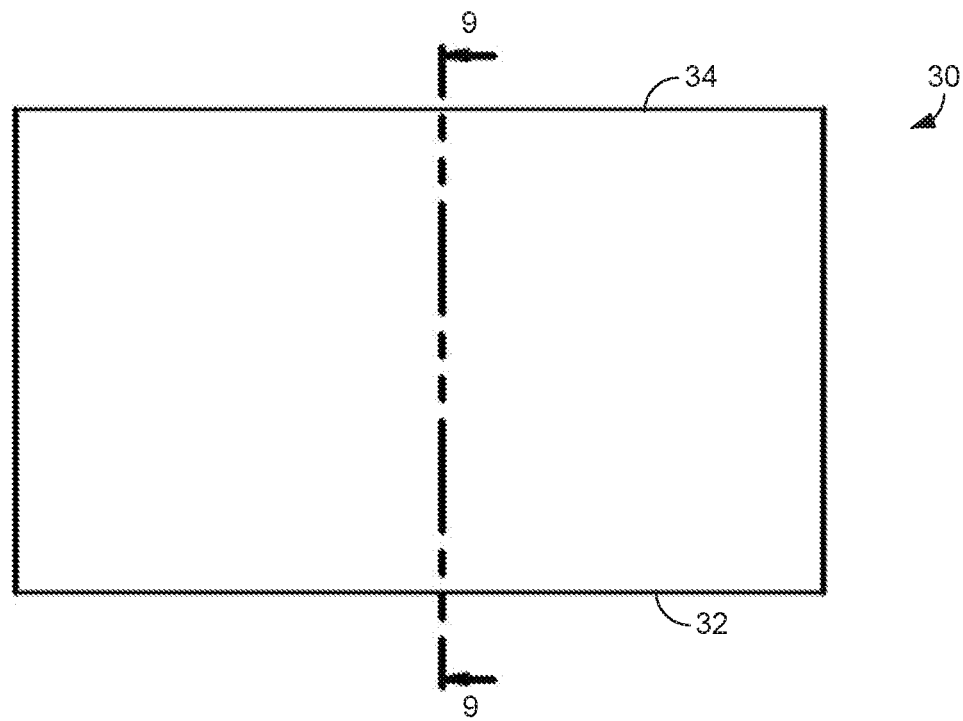
FIG. 8 is a side view of the cap of FIG. 5.
Figure 9:
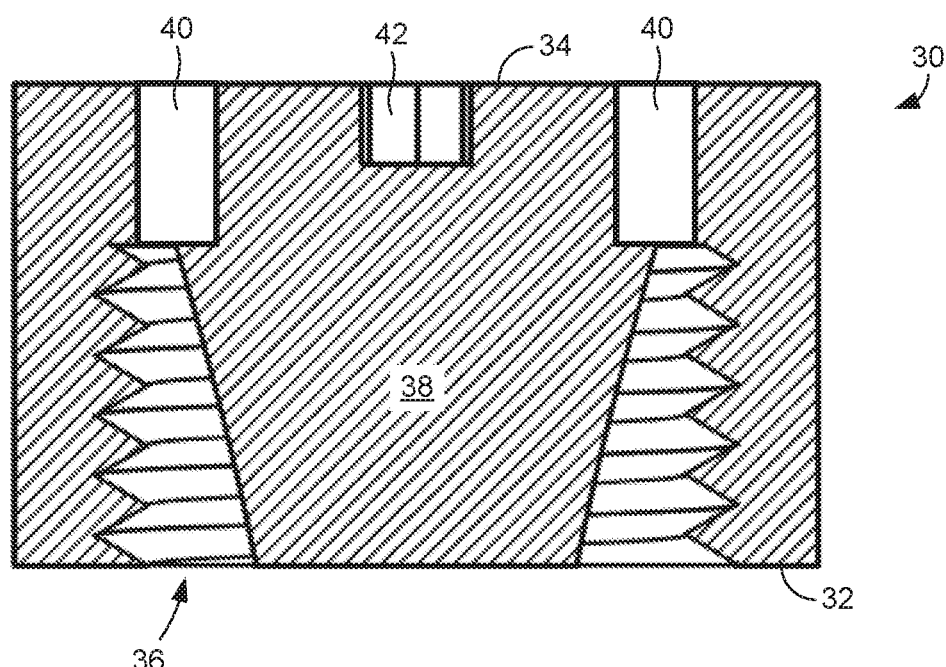
FIG. 9 is a side cross-sectional view of the cap of FIG. 5 taken along line 9—9 shown in FIG. 8.

As is illustrated FIGS. 5, 6, and 9, the cap 30 further includes suture passages 40 that extend through the top surface 34 of the cap to the threaded circular opening 36. In the illustrated embodiment, the passages 40 are arcuate so as to extend along the periphery of the threaded circular opening 36. As described below, the ends of a suture that have passed through the base 10 can further be passed through the threaded circular opening 36 of the cap and its passages 40 to facilitate anchoring of the sutures and a graft tendon to which the suture is attached. Also illustrated in FIGS. 5 and 6 is a star-shaped central opening 42 that can receive a tool, such as a star-shaped wrench or driver, to enable secure threading of the cap 30 onto the base 10.

Figure 10:
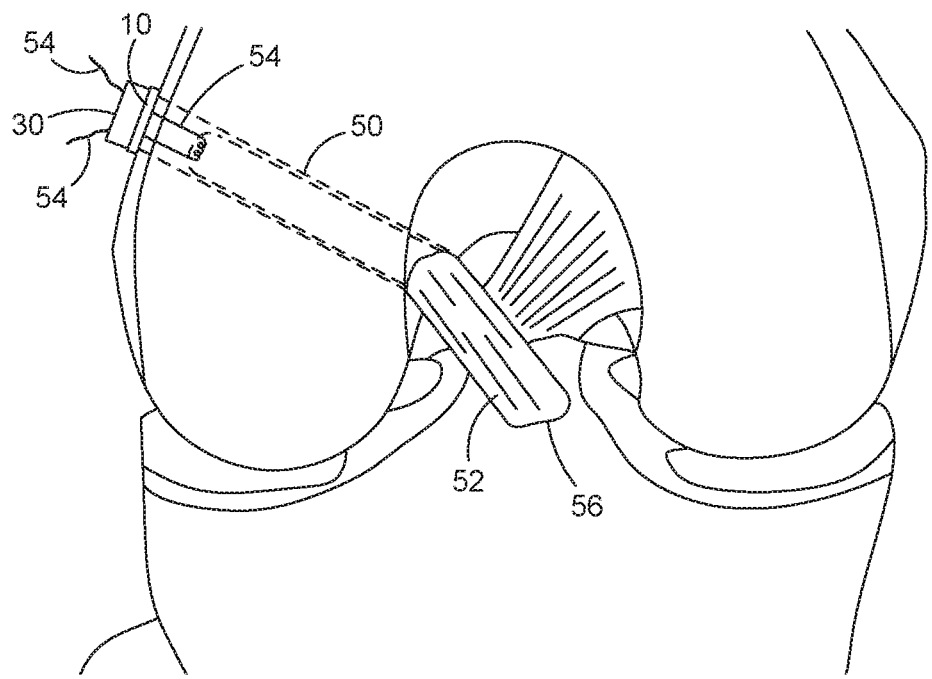
FIG. 10 is a front view of a knee joint that illustrates use of the reversible anchoring device comprised of the base and cap of FIGS. 1-4 and 5-9, respectively.
Figure 11:
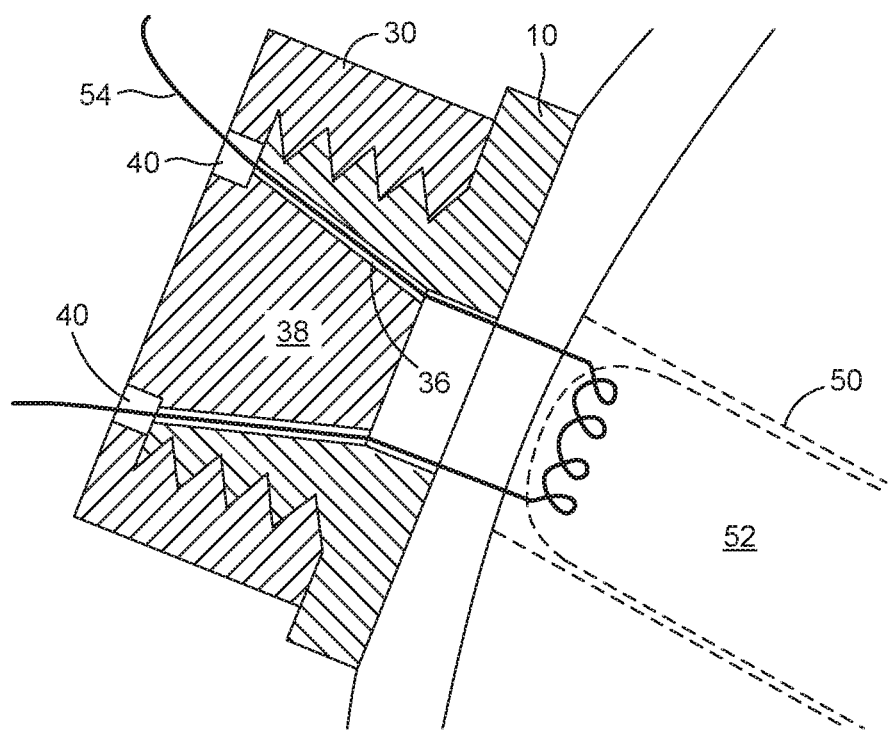
FIG. 11 is a detail view of the anchoring device shown in FIG. 10, illustrating the device positioned on a surface of the femur.

FIGS. 10 and 11 illustrate the anchoring device, including its base 10 and cap 30, in use in a suspensory fixation ACL reconstruction procedure. As shown in FIG. 10, a passage 50 has been formed (e.g., drilled) through the femur so as to enable a graft tendon 52 to be pulled into the femur with a suture 54. In some embodiments, the graft tendon 52 can be folded over on itself to form a loop and the suture 54 can be passed through the loop. In other embodiments (and as shown in FIGS. 10 and 11), the suture 54 can be threaded through an end of the graft tendon 52. With further reference to FIG. 10, a passage 56 has also been formed through the tibia so that the graft tendon 52 can also be pulled into the tibia.

Once the graft tendon 52 has been pulled through the passage 50 in the femur to a desired extent, the ends of the suture 54 can be passed through the internal passage 18 of the base 10 and the base can be positioned on top of the opening of the femur passage 50, for example, using a cannula or other hollow tubular instrument. As shown best in FIG. 11, the base 10 can be positioned so that its bottom surface 16 contacts the outer surface of the femur.

Each end of the suture 54 can also be passed through the threaded circular opening 36 of the cap 30 and through one of the sutures passages 40 that extend from that opening to the top surface 34 of the cap. The cap 30 can then be delivered to the base 10 also using a cannula or other hollow tubular instrument. The cap 30 can then be threaded onto the base 10 so that the threaded shaft 14 of the base threads into the threaded circular opening 36 of the cap. In some embodiments, this can be performed using a wrench or driver having a star-shaped tip that matches the central opening 42 formed in the top of the cap 30. Once the cap 30 is tightly threaded onto the base 10, the lengths of suture 54 will be securely clamped between the frustoconical member 38 of the cap and the frustoconical portion 22 of the internal passage 18 of the base.

At this point, the opposite end(s) of the graft tendon 52 can be pulled through the tibia with a desired degree of tension and then anchored within or outside of the tibia.

The above-described anchoring device exhibits several advantages over conventional suspensory button anchoring devices. First, because of its simplicity, the disclosed anchoring device is both relatively inexpensive to produce and relatively simple to use. In regard to use, the anchoring device need not be passed through the femur and deployed while within the bone like conventional anchoring devices. Second, unlike current devices, the disclosed anchoring device is less likely to loosen after fixation. Third, the disclosed anchoring device is reversible. Specifically, if it is desired to change the position of the graft tendon after fixation, the cap 30 can be loosened, the graft tendon can be repositioned, and the cap can be retightened.

Figure 12:
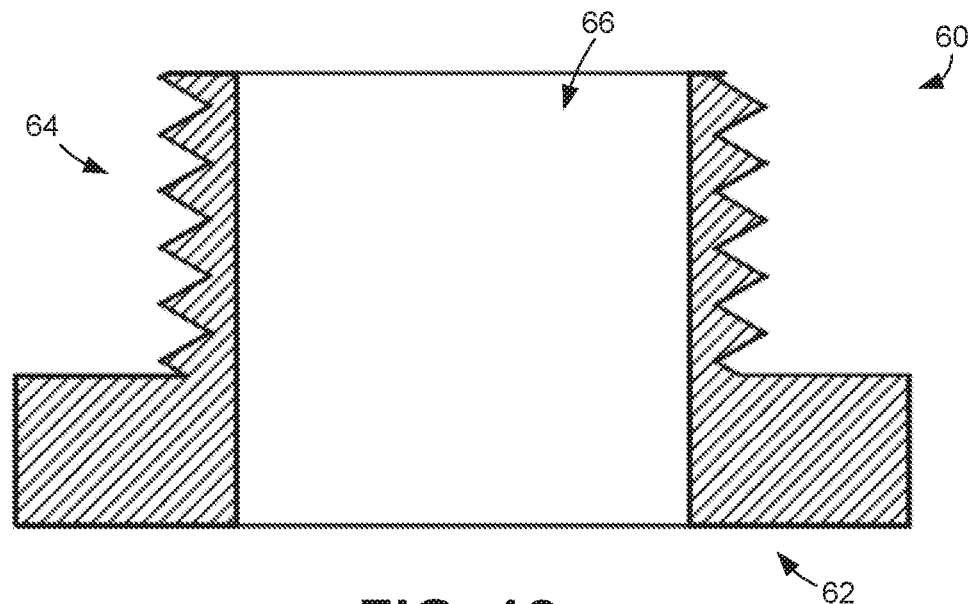
FIG. 12 is a side cross-sectional view of an alternative embodiment of a base of a reversible anchoring device.
Figure 13:
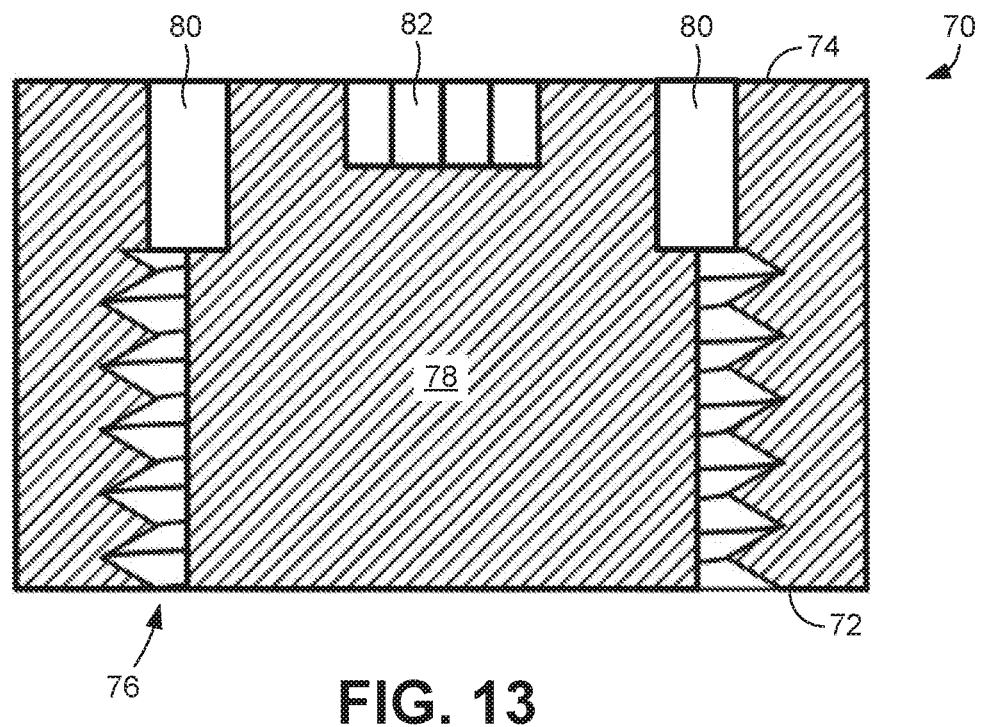
FIG. 13 is a side cross-sectional view of an alternative embodiment of a cap designed to be used with the base of FIG. 12.

FIGS. 12 and 13 illustrate an alternative base 60 and cap 70, respectively, that can be used to form an alternative reversible anchoring device. Beginning with FIG. 12, the base 60 is similar in many ways to the base 10 shown in FIGS. 1-4. Accordingly, the base 60 includes a hexagonal head 62 from which extends a threaded shaft 64. The base 60 further includes an internal passage 66 that extends through the head 62 and the shaft 64. Unlike the base 10, however, the passage 66 comprises a single, generally cylindrical passage (i.e., no frustoconical portion).

Referring next to FIG. 13, the cap 70 is similar in many ways to the cap 30 shown in FIGS. 5-9. Accordingly, the cap 70 is generally cylindrical and includes a first or bottom surface 72, a second or top surface 74, and threaded circular opening 76 that is adapted to thread onto the threaded shaft 64 of the base 60. The threaded circular opening 76 extends into the body of cap 70 a distance approximately three-quarters of the way to the top surface 74. Unlike the cap 30, the cap 70 includes a generally cylindrical central member 78 (not a frustoconical member) that is positioned within the threaded circular opening 36 and extends from the bottom of the opening to the bottom surface 72 of the cap. This member 78 is sized and configured to be received by the internal passage 66 of the base 10 with little clearance between the member and the passage.

The cap 70 further includes suture passages 80 that, like the passages 40 of the cap 30, extend through the top surface 74 of the cap to the threaded circular opening 76. In addition, the cap 70 includes a star-shaped central opening 82 that can receive a tool, such as a star-shaped wrench or driver, to enable secure threading of the cap onto the base 60.

The invention claimed is:

1. A reversible anchoring device comprising:
a base having a head, a cylindrical threaded shaft having a constant outer diameter along its entire length that extends from the head, and an internal passage that extends through the entire length of the base along a longitudinal direction of the base, a first portion of the internal passage extending through the head and a second portion of the internal passage extending through the cylindrical threaded shaft; and
a cap having a top surface, a bottom surface, a cylindrical threaded opening formed in the bottom surface and extending part of a length of the cap adapted to thread onto the cylindrical threaded shaft of the base, and a suture passage that extends from the top surface of the cap to the cylindrical threaded opening through which a suture can pass, the cap further having a central member positioned within the cylindrical threaded opening that is configured to be received within the second portion of the internal passage of the base.

2. The anchoring device of claim 1, wherein the second portion of the internal passage is frustoconical.

3. The anchoring device of claim 2, wherein a diameter of the frustoconical second portion expands in a direction away from the head.

4. The anchoring device of claim 2, wherein the first portion of the internal passage is cylindrical.

5. The anchoring device of claim 2, wherein the central member is frustoconical and is adapted to be received in the frustoconical second portion of the internal passage of the base with little clearance between the member and the passage so as to be configured to securely clamp a suture positioned between the member and the passage.

6. The anchoring device of claim 5, further comprising a central opening in the top of the cap that is adapted to receive a tip of a wrench or driver that can be used to thread the cap onto the base.

7. The anchoring device of claim 1, wherein the cap comprises two suture passages that extend from the top surface of the cap to the cylindrical threaded opening through which sutures can pass.

8. The anchoring device of claim 1, wherein the suture passage is arcuate.

9. A method for suspensory fixation of a graft tendon in an anterior cruciate ligament (ACL) reconstruction procedure, the method comprising:
- forming a passage through the femur;
- pulling a graft tendon into the femur passage using a suture;
- passing the suture through a base passage formed in a base of an anchoring device, the base passage extending through the entire length of the base;
- positioning the base on the surface of the femur over an opening to the femur passage without inserting the base into the femur passage;
- passing the suture through a cap passage formed in a cap of the anchoring device; and
- threading the cap onto the base to position a central member provided within the cap into the base passage in close proximity to surfaces of the base passage so as to securely clamp the suture between the central member of the cap and the base;
- wherein no component of the anchoring device is positioned within the femur passage.

10. The method of claim 9, wherein the base passage includes a frustoconical portion.

11. The method of claim 10, wherein the central member of the cap is frustoconical and is adapted to be received by the frustoconical portion of the base passage.

12. A reversible anchoring device comprising:
- a base having a head, a cylindrical threaded shaft having a constant outer diameter along its entire length that extends from the head, and an internal passage that extends through the entire length of the base along a longitudinal direction of the base, a first portion of the internal passage extending through the head and being cylindrical and a second portion of the internal passage extending through the cylindrical threaded shaft and being frustoconical, wherein a diameter of the frustoconical second portion expands in a direction away from the head; and
- a cap having a top surface, a bottom surface, a cylindrical threaded opening formed in the bottom surface and extending part of a length of the cap adapted to thread onto the cylindrical threaded shaft of the base, and a suture passage that extends from the top surface of the cap to the cylindrical threaded opening through which a suture can pass, the cap further having a central frustoconical member positioned within the cylindrical threaded opening that is configured to be received within the frustoconical second portion of the internal passage of the base with little clearance between the member and the passage so as to be configured to securely clamp a suture positioned between the member and the passage, the cap further comprising a central opening in the top of the cap that is adapted to receive a tip of a wrench or driver that can be used to thread the cap onto the base.

13. The anchoring device of claim 12, wherein the cap comprises two suture passages that extend from the top surface of the cap to the cylindrical threaded opening through which sutures can pass.

14. The anchoring device of claim 13, wherein the suture passages are arcuate.

* * * * *